United States Patent [19]

Lather et al.

[11] 4,182,154

[45] Jan. 8, 1980

[54] INITIALIZING ULTRASONIC TEST EQUIPMENT WITH A PARTICULAR REFERENCE ELEMENT

[75] Inventors: Dieter Lather, Rheurdt; Wolfgang Terschüren, Mülheim; Kurt Hannöschock, Sonsbeck; Günter Simoneit; Karl Ries, both of Mülheim, all of Fed. Rep. of Germany

[73] Assignee: Mannesmann Aktiengesellschaft, Duesseldorf, Fed. Rep. of Germany

[21] Appl. No.: 878,240

[22] Filed: Feb. 16, 1978

Related U.S. Application Data

[63] Continuation-in-part of Ser. No. 822,919, Aug. 8, 1977, abandoned.

[30] Foreign Application Priority Data

Aug. 6, 1976 [DE] Fed. Rep. of Germany ....... 2635982

[51] Int. Cl.² ............................................ G01N 29/00
[52] U.S. Cl. ..................... 73/1 DV; 367/13
[58] Field of Search ............ 73/1 DV, 609, 627, 632, 73/644; 340/8 FT, 5 C

[56] References Cited

U.S. PATENT DOCUMENTS

| | | | |
|---|---|---|---|
| 2,490,452 | 12/1949 | Mason | 73/1 DV |
| 3,014,198 | 12/1961 | Harris | 340/8 FT |
| 3,665,379 | 5/1972 | Trott | 340/5 C |
| 4,038,629 | 7/1977 | van der Burgt et al. | 340/8 FT |

*Primary Examiner*—Stephen A. Kreitman
*Attorney, Agent, or Firm*—Smyth, Pavitt, Seigemund, Jones & Martella

[57] ABSTRACT

A tubular sleeve with reflector body, water ingress and venting openings is used to produce specific echoes of a test signal launched by an inserted transducer. Amplitude and transit times of the element serve as a transferable standard.

6 Claims, 2 Drawing Figures

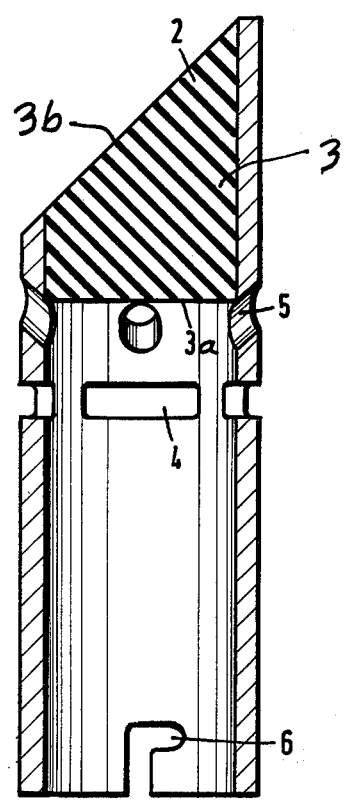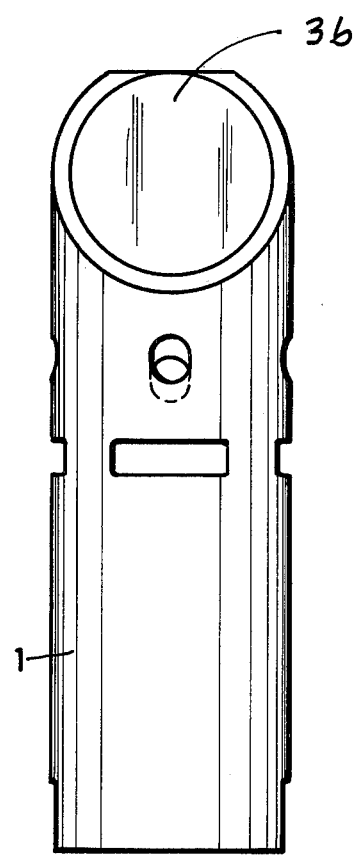

INITIALIZING ULTRASONIC TEST EQUIPMENT WITH A PARTICULAR REFERENCE ELEMENT

This is a continuation-in-part of application Ser. No. 822,919 filed Aug. 8, 1977, now abandoned.

BACKGROUND OF THE INVENTION

The present invention relates to a reference element to be used for adjusting, calibrating and initializing ultrasonic test equipment for inspecting structural materials.

Extensive equipment for the non-destructive testing of structural material includes, for example, a test stand having at least one, often many, ultrasonic test heads which are to be coupled to the test object for purposes of inspecting the object as to the texture of its interior for purposes of detecting any flaws, inclusions, defects, etc. It is, of course, required that the various test heads in this stand be particularly oriented to the test object as it is going to pass through the stand. Moreover, it is required that the test electronics be adjusted to the particular conditions under which the test is conducted. The test electronics involves particularly the electronic circuitry which processes the ultrasonic signals being received, and that circuitry must be adjusted to the particular conditions under which the test is conducted. The geometric dimensions and propagative properties of the object to be tested and the specific zone therein to be inspected require or make it advisable to launch test pulses along a particular path and into the object for interaction therewith; the interaction may produce a return pulse to be picked up by the same or companion transducer. Depending on the particular conditions, a return pulse may, for example, be an echo from a boundary or an echo from a flaw. The amplitude and time of occurrence of such a return pulse is determined by the propagative properties of the material and by the geometry of the propagative properties. The amplitude is in addition determined by the conditions of its specific production such as the size and orientation of a flaw. On the other hand, the transducer listening to such a response will inevitably pick up noise. It follows therefore that for a specific test task a response to be recognized as a response to an ultrasonic test signal, must have a minimum amplitude to distinguish it from noise, and it must occur wihtin a prescribed period. Thus, the electronics processing the received transducer signal must be adjusted to be responsive to signals of a particular period only (looking window). These are parameters which have to be adjusted before the test can begin.

In application Ser. No. 782,451, filed March 29, 1977, now U.S. Pat. No. 4,106,326, a procedure of initialization, adjusting and calibration is described in detail. This initialization procedure involves in the essence a test body having many similar features as the object to be tested, including in particular the geometry for a test beam path and including further simulated errors so that timing and amplitude of return response signals can be ascertained. For this, a special electronics is used in conjunction with the heads which are positioned and oriented in relation to the test object in exactly the same manner they are expected to be adjusted and oriented later in the test stand. This particular electronics is not the same as the electronics to be used in the test stand but is provided just for ascertaining the necessary parameters under which any electronics is to operate. This initialization electronics will in the following be called preparatory electronics. It will respond to return signals resulting from the interaction of that test pulse with the test body, and the timing and amplitude of that return pulse is ascertained. In conjunction therewith, the period in which such a return signal may occur is ascertained. This alone, however, is not sufficient because as stated, the heads will be installed later in the test stand though under similar orientation and spacing adjustment, but for cooperation with the same type of, but actually a different test stand electronics. Therefore, the initialization procedure requires a standard and reference element to be coupled to the various heads and to be used to invoke a specific response signal to a test pulse. That test pulse launched into the reference body produces a response occurring following a specific transit time and at a particular amplitude, on the basis of the adjusted preparatory electronics. Thereafter, the reference element is used again on the test heads as they are being installed in the final test stand but now in conjunction with the test stand or operational electronics proper; a test signal is launched into this reference body, and its response is being ascertained by and in the test electronics. That response in conjunction with the response previously ascertained when that reference element was used in conjunction with the preparatory electronics, is now used to finally determine the specific parameters of the test electronics in the test stand.

DESCRIPTION OF THE INVENTION

It is an object of the present invention to improve the adjusting, initialization and calibration procedure of ultrasonic test equipment for the nondestructive tests of structural materials, by the use of a new reference element.

In accordance with the preferred embodiment of the present invention, it is suggested to use as a reference element a tube having one end oblique, preferably at a 45° angle with respect to the tube's axis, and to partially fill that tube at the oblique end with a reflector body having an inner surface of, for example, 90° to the axis which inner surface is exposed to the unfilled interior of the tube. The reflector body has a correspondingly oblique surface at the oblique tube end. The tube has water ingress and venting openings and means for connecting the other end of the tube to the test equipment. The reference element can be used for calibration purposes as described to establish in a simple manner reproducible conditions under which are produced specific responses to an ultrasonic test signal launched via a head when inserted in the tube, toward the reflector body. The reference element in particular can be used as a calibration element and for the purpose outlined above. However, it was found that this particular test element can be used also as a test body obviating in cases the need for a test object-like replica. In any event, the reference element becomes a standard by means of which particular conditions are transferred from one electronics to another one; the standard serves to establish an identical environment for specific reference signals, which can be used as modifier for other parameters.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a front view of a reference element in accordance with the preferred embodiment of the present invention;

FIG. 2 is a section view along lines 2 in FIG. 1.

Proceeding now to the detailed descriptions of the drawings the reference element illustrated includes a sleeve 1 having an oblique rear end and a circular front end. A reflecting body 2 made of a sound attenuating material, such as rubber, is inserted in sleeve 1 and is flush with that oblique front end, having an oval boundary and surface 3b accordingly. The oval, outer and exposed surface 3b of body 2 has a 45° angle to the axis of the sleeve. Reference numeral 3a denotes the inner surface of reflector body 2 being exposed to the unfilled interior of the sleeve 1. That particular surface 3a extends at right angles to the axis of the sleeve and constitutes the primary reflecting surface of that reference element.

The sleeve 1 has, in addition, a plurality of elongated slots, there being altogether four such slots 4. A plurality of oblique venting bores 5 are located between the water ingress slots 4 and the reflector body. Each bore 5 has in fact an internal boundary which in each instance is tangent to the boundary of the reflector surface 3a. The bores 5 slope upwardly at a 45° angle. The other end of the sleeve 1 is provided with two angular slots 6 which face each other across the diameter of the sleeve. These slots are provided for bayonet-like coupling of the reference element to a clamping sleeve or the like so that the reference elements can be firmly connected to structures from which extends an ultrasonic test head to be inserted into tube 1.

The reference element as described is used generally in that it is connected to a test head in the stated manner, and the transducer of the head is, for example, operated at first in the transmitter mode followed by a switchover to the receive mode. The interior of the sleeve has been filled with water through the openings 4 and the venting openings 5 to make sure that water will fill the tube entirely and will, in fact, be in direct contact with the surface 3a. The length of the sleeve and particularly the distance of surface 3a from the other end of the sleeve (through which the transducer will project), is selected to define a particular acoustical path.

The inserted transducer emits an ultrasonic pulse which will be reflected in parts by the front surface 3a of the reflector body 2 and will be bounced back to be received by the transducer. In the meantime that transducer may been switched over as far as its output electronics is concerned to operate in the receive mode. Alternatively, there may be two transducers in the head, one operating in the transmit and the other one in the receive mode.

The ultrasonic beam which was emitted by the test head passes through the water in axial direction. It should be noted that the transducer to which this particular element is connected has been adjusted to assume a particular orientation angle in the test head and will, ultimately, be oriented at that angle to the test object or the objects to be tested. The reference element as described is placed on the transducer independently from that orientation, i.e. the axis of the reference element (sleeve 1) will always be oriented to the transducer in the same angle, regardless of the particular angular adjustment of the inserted transducer in the head, so that irrespective of the orientation of the transducer in the test stand, an ultrasonicbeam is always emitted into and along the axis of sleeve 1 and the return echo will follow that same path in the opposite direction. An example for such a head mount is, for example, disclosed in copending application Ser. No. 856,223, filed Dec. 1, 1977.

It should be noted that a portion of the ultrasonic beam enters the test body 2 and is reflected to some extent at the 45° outer surface 3b and towards the sleeve wall. Some of the radiation will bounce back, but generally speaking, that portion of the radiation is dissipated, so that very little, if any, will return to the receiving transducer.

Proceeding now to the specific use of the reference element as illustrated for purposes of calibrating and initializing electronic test equipment. In a calibration and separate test room, a test head is mounted in a particular orientation with respect to a test body into which a test pulse is launched, and from which a response resulting, for example, from a simulated error or flaw in the test body is expected. That test head and particularly the transducer operating in the receive mode is connected to a particular calibration or preadjust electronics. That preadjust electronics will be specifically adjusted; for example, with respect to a gating period, i.e. the beginning and end of a looking window period, adjusted phase or delay relative to the time of launching the test pulse, to having a particular time of occurrence of the flaw echo. Moreover, the flaw echo appears in the pre-adjust electronics at a particular amplitude.

Now, the reference element described is placed on such a test head from which the test body has been removed, and again a pulse is launched but now into that reference element. The pre-adjust electronics has remained adjusted from the previous test involving the test body, for example, as to signal gain. Now, there is a particular echo resulting from a reflection of that pulse by surface 3a. That reflection is specifically ascertained as to its transit time from the time of launching the test pulse into the reference element and as to its amplitude. The transit time may be $T_1$ and the amplitude of that echo may be $A_1$. Later, the particular test head is installed in the test stand under the previously determined orientation and it is connected to the test electronics to be used for testing structural material. Again, the same reference element as described and illustrated is placed on the test head and the same kind of pulse is launched. The echo of that pulse on surface 3a is determined as to its transit time and as to its amplitude, but now on the basis of the test electronics in the test stand. The transit time of the echo as required under these conditions may be $T_2$ and the amplitude of the echo may be $A_2$. Due to differences in the electronics, the amplitudes $A_1$ and $A_2$ may differ greatly.

Any deviation in these values ($A_2$, $T_2$) from those ascertained in the pre-adjust electronics ($A_1$, $T_1$) are used for adjusting the relevant test electronics parameters. In particular, the beginning and end of any looking window and gating period is adjusted as to its timing, onset and termination by the time differential $T_2 - T_1$. The amplitude response in the test electronics, particularly the threshold level for such a response, is now adjusted in the test electronics on the basis of the factor $A_2/A_1$.

It can thus be seen, that the reference element is used as a transferable standard in the sense that it offers very specific and identical conditions to the same or to different heads operated at different times under similar but not identical conditions. Standard permits the adapting of different conditions to each other to become operationally comparable. The reference element upon being mounted to the test head in the calibration room as well as in the final test stand will, in fact, be immersed in water, and the water will enter the interior of the tube through the bores 4. The water will fill the interior of the tube, and any air that may be trapped will escape from the interior through the upward slanting ducts 5 so that water will with certainty contact the surface 3a.

The invention is not limited to the embodiments described above but all changes and modifications thereof not constituting departures from the spirit and scope of the invention are intended to be included.

We claim:

1. In a method of preparing ultrasonic test equipment having at least one transducer operating in conjunction with a coupler fluid, the test equipment requiring adjustment on the basis of reference signals, placing a reference element onto and over the transducer, the element being comprised of a cylindrical sleeve or tube having an axis, one oblique end and a partially hollow interior adjacent the opposite end of the sleeve at which said transducer is inserted, further having openings for ingress of water when placed in the coupler fluid and upon insertion of the transducer into the hollow interior of the sleeve the reference element being further comprised of:
   a reflector body in the sleeve and disposed adjacent said oblique end and having a correspondingly oblique surface, the reflector body having another interior surface facing the hollow interior of the sleeve and being spaced from the said opposite end of the sleeve at a particular distance; the reference element having additionally venting openings adjacent to the other surface which would open to the hollow interior of the sleeve; and
   using the reference element for the generation of said reference signals in and by means of said transducer.

2. In a method as in claim 1 wherein the venting openings extend slantingly upward from the other interior surface of the reflection body.

3. In a method as in claim 1 wherein the other interior surface extends at right angles to the axis of the sleeve.

4. Reference element for adjusting an ultrasonic test equipment having transducer operating in conjunction with a coupler fluid, the test equipment requiring adjustment on the basis of reference signals, a solid reference element comprising a cylindrical sleeve or tube having an axis, one oblique end and a partially hollow interior adjacent the opposite end of the sleeve, further having openings for ingress of water when placed in the coupler fluid and upon insertion of the transducer into the hollow interior of the sleeve;
   a reflector body in the sleeve and disposed adjacent said oblique end and having a correspondingly oblique surface, the reflector body having another interior surface facing the hollow interior of the sleeve and being spaced from the said opposite end of the sleeve at a particular distance; and
   venting openings adjacent to the other surface which would open to the hollow interior of the sleeve.

5. Reference element as in claim 4, wherein the venting openings extend slantingly upward from the other interior surface of the reflection body.

6. Reference element as in claim 5, wherein the other interior surface extends at right angles to the axis of the sleeve.